(12) United States Patent
Daners et al.

(10) Patent No.: US 7,238,181 B2
(45) Date of Patent: Jul. 3, 2007

(54) HIGH-FREQUENCY SURGERY GENERATOR

(75) Inventors: Felix Daners, Schaffhausen (CH);
Pavel Novak, Stetten (CH)

(73) Assignee: Storz Endoskop Produktions GmbH (DE)

( * ) Notice: Subject to any disclaimer, the term of this patent is extended or adjusted under 35 U.S.C. 154(b) by 83 days.

(21) Appl. No.: 10/971,418

(22) Filed: Oct. 22, 2004

(65) Prior Publication Data
US 2005/0137589 A1   Jun. 23, 2005

Related U.S. Application Data

(63) Continuation of application No. PCT/DE03/01365, filed on Apr. 28, 2003.

(30) Foreign Application Priority Data
Apr. 26, 2002  (DE) ................ 102 18 893

(51) Int. Cl.
*A61B 18/18* (2006.01)
(52) U.S. Cl. ............ 606/39; 606/38; 606/40
(58) Field of Classification Search ........... 606/32, 606/33, 34, 35, 39, 40, 41, 45, 49
See application file for complete search history.

(56) References Cited

U.S. PATENT DOCUMENTS 4,114,623 A   9/1978 Meinke et al. ......... 128/303.14
4,818,954 A * 4/1989 Flachenecker et al. ...... 331/183

FOREIGN PATENT DOCUMENTS

DE  100 13 795   10/2001
WO  WO 93/03677   3/1993

\* cited by examiner

*Primary Examiner*—Lee S. Cohen
(74) *Attorney, Agent, or Firm*—St. Onge Steward Johnston & Reens LLC

(57) ABSTRACT

A high-frequency generator for high-frequency surgery comprises a power generator for supplying high frequency energy at a base frequency. A standardizing factor is determined, with which an output variable from the power generator must be scaled in order to attain a given desired value. Furthermore, harmonics of the base frequency are determined from the output variable and scaled using this factor. By means of an input, the thus obtained signal now controls the output power of the generator. With this arrangement, a reliable first cut may be performed on various kinds of tissue without occurrence of any coagulation.

10 Claims, 2 Drawing Sheets

HIGH-FREQUENCY SURGERY GENERATOR

CROSS REFERENCE TO RELATED APPLICATIONS

This application is a continuation of pending International Application No. PCT/DE03/01365 filed on Apr. 28, 2003, which designates the United States and claims priority from pending German Application No. 102 18 893.9 filed on Apr. 26, 2002.

BACKGROUND OF THE INVENTION

The invention relates to a generator for power generation for high-frequency surgery. In high-frequency surgery, human or animal body tissue is cut or coagulated by means of an electric current. High-frequency surgery is usable with extreme advantage, particularly with endoscopic operating techniques.

1. Field of the Invention

It is the purpose of high-frequency surgical generators to provide electrical energy for high-frequency surgery in such manner that a desired operation result is obtained. In order to minimize muscle and nerve irritation, high-frequency surgical generators supply high-frequency energy in a frequency range above 300 kHz. This high-frequency energy is usually introduced into tissue by means of an electrode. Strong heating of the tissue surrounding the electrode occurs at the site of introduction. If high energy is supplied within a short period of time, this results in a vaporization of cell fluid and a bursting of cells, so that the group of cells around the electrode disintegrates. The electrode can move almost freely through the tissue. If less energy is supplied for a long period of time, this results in a coagulation of the tissue, i.e. to congealing of protein. In this case, the cells die off and become a viscous mass.

As far as the introduction of high-frequency energy is concerned, basically a distinction is made between two arrangements.

In a monopolar arrangement, a cutting or coagulating electrode having a small surface for introducing current is disposed at the site of operation, and a "neutral" electrode of large surface for conducting current away is disposed at a different site on the body of a patient. Here the electrode surface is dimensioned to be large enough for no appreciable heat to be developed at the electrode.

A bipolar arrangement comprises a divided electrode with which an introduction of current and a conducting away of current occur at the site of the operation.

Dosing of the energy is of great importance, because this directly affects the result of the operation. If the generator supplies too little energy, then no cutting is possible, and if too much energy is supplied, then the cut edges are strongly coagulated, which in turn leads to difficult healing or increased risk of infection.

Therefore, it is the aim to introduce into the body as little energy as possible for a pure cutting process, and the minimum amount of energy needed for coagulation for a combined cutting and coagulating process.

2. Description of the Prior Art

For minimization of this energy, the U.S. Pat. No. 4,114,623 discloses a method for regulating the generator current by observations of the electric arc appearing during cutting.

Here a start of cutting, or a transition to a different kind of tissue having different electrical properties, presents a special problem. Because a transition to a different kind of tissue involves almost the same problem as is set by a start of cutting, reference will be made in the following to only the start of cutting.

If cutting is started with too high power, an undesired coagulation will already occur at the site of cutting. In order to minimize this coagulation, DE 38 15 835 A1 proposes that the generator output voltage be limited. This prevents a first cut from being made with too high generator power. If, instead of this, a first cut is made with too low power, this will lead to no cutting process being performed by penetration of the electrode into the tissue, but rather to an undesired coagulation of the tissue surface. This will also make a further first cut more difficult. In order to ensure a safe first cut without dependence on the tissue, DE 41 35 184 A1 proposes that an increased generator power be supplied at the start of making a first cut. This increased emission of power can then be lowered to the value normally needed for cutting when an electric arc is detected.

Both measures proposed here for optimizing a start of cutting exclude each other. Thus, one the one hand, to avoid a coagulation by too high a generator power, the generator power can be limited, which however can lead to a coagulation in case no first cut is made. On the other hand, a first cut can be made with increased power, whilst accepting an occurrence of coagulation.

BRIEF SUMMARY OF THE INVENTION

The invention is based on the object of providing a high-frequency generator for surgery, which ensures the making of a safe first cut without coagulation at the site of the first cut, irrespective of the kind of tissue.

In accordance with the invention, this object is achieved by a high-frequency generator for high-frequency surgery, comprising:

a power generator for supplying high-frequency energy at a base frequency;

a sampling tap for coupling out a variable to be measured, corresponding to an output voltage or an output current; and at least one input for setting a magnitude of an electrical output parameter selected from an output voltage, an output current, and an output power;

wherein a first filter is provided for selecting harmonic frequency components above a base frequency from the variable to be measured;

a standardizing circuit is provided for determining a standardizing factor k in such manner that the measured variable or a proportion of the basic frequency in the measured variable, multiplied by the standardizing factor, corresponds to a given desired value;

means are provided for scaling the harmonic frequency components with the standardizing factor k; and for controlling the power generator, a signaling of scaled harmonic frequency components to the power generator by means of the input is provided in such manner that with an increase of an amplitude of the scaled harmonic frequency components, the output voltage, the output current or the output power of the power generator is reduced.

The high-frequency generator according to the invention comprises at least one power generator for delivering high-frequency energy at a base frequency. A sampling tap serves for coupling out a variable to be measured which corresponds to the output voltage or the output current. Furthermore, an input is provided for presetting an electrical output variable such as output voltage, output current and output power. Basically, these output variables can be also related to the output power. Thus, for a certain load impedance, and a given output voltage or given output current, a definite output power is obtained. It is the magnitude of the power introduced into the tissue that actually determines the physical result, i.e. a cutting or coagulation.

According to the invention, a standardizing circuit is provided for determining a standardizing factor k in such manner that a measured variable. multiplied by this standardizing factor corresponds to a given desired value. Instead of a measured variable, preferably the proportion of the base frequency in the measured variable may be used. For this, a suitable filter must be provided. The use of the base frequency is of advantage when a high proportion of harmonic signal components is present, because otherwise these can falsify the measurement result. Furthermore, a first filter is provided for selecting harmonic frequency components above the ground frequency from the measured variable. These harmonic frequency components are scaled using a means for scaling with the previously determined standardizing factor k. The harmonic frequency components scaled in this manner are then transmitted to the power generator via the input. There follows a control of the power generator in such manner that an increase of the amplitude of the scaled harmonic frequency components causes a reduction of the output power, or even of the output voltage or output current of the power generator.

The first filter may consist also of a plurality of filters. In this case the actual transmission function is of importance. Thus, optionally a single harmonic, for example at the 3 fold or 5 fold base frequency may be selected. In the same manner, a plurality of these harmonics, or even wider frequency bands may be selected. A particularly simple embodiment is obtained when the filter is designed to be a high-pass filter which suppresses the base frequency and passes all frequencies above the base frequency. An optimal matching of the filter is made taking into account the spectral distribution of the output signal of the generator. Thus, for example, in the case of a non-symmetric generator output signal in which the odd multiples of the base frequency have relatively high amplitudes, it may be expedient to design the filter to suppress these. Thus, basically the filter should be dimensioned so that a frequency range is selected in which the generator output signal—without a cutting operation being performed—has relatively low spectral components, but in which, because of the electric arc occurring during cutting, distinctly evaluative spectral components are present. According to experience, these occur at odd multiples of the base frequency. With the design according to the invention, it is of importance that an independence from the amplitude of the generator signal itself be attained by means of the described scaling. Thus, a satisfactory first cut can be made with a multiplicity of electrode geometries independently from the cross-sectional area of the electrode.

In order to obtain a good regulating performance, it is of advantage for the high frequency generator itself, or a line unit in case it is driven by a line unit, to have a high regulating speed, so that a response to the signals transmitted via the input may be rapid. Tests have shown that a time constant of the generator of less than 1 ms is of advantage.

In a particularly advantageous embodiment of the invention, the standardizing circuit has a first rectifier for determining the peak value of the variable to be measured. With this, the standardizing factor k indicates the value to which the peak value of the variable to be measured must be scaled in order that it may attain the given desired value. With this arrangement it is particularly expedient to select the base frequency from the variable to be measured before performing the standardization, because then brief interference signals that may originate for example from high-frequency harmonics, or even from noise, are suppressed and do not affect the peak value measurement.

Another advantageous embodiment of the invention has a first rectifier in the standardizing circuit for determining the effective value, or optionally the mean value, of the variable to be measured. With this, the standardizing factor k indicates the value to which the effective value of the measured variable must be scaled in order that it may attain the given desired value.

In another advantageous embodiment of the invention, the standardizing circuit comprises a regulator circuit. This diminishes the variable to be measured by means of a first settable attenuating member, so that it corresponds to a given desired value.

In the present explanations, the terms attenuating member, diminishing means, or diminishing are used. Of course, these terms denote a scaling in the general sense, and also an amplification.

Another advantageous embodiment of the invention consists in the first filter for selecting harmonic frequency components being disposed in series to follow the first settable attenuating member. With this, the attenuating member diminishes the overall variable to be measured, including the harmonic frequency components contained therein. Thus, only one single attenuating member is needed for determining the scaling factor, and for scaling the harmonic frequency components.

A further advantageous embodiment of the invention consists in a second adjustable attenuating member being provided to diminish the harmonic frequency components, this attenuating member being controlled in parallel with the first settable attenuating member. Thus, the attenuations by the attenuating members correspond to each other; that is, both signal paths are subjected to the same attenuation. By being divided into two separate signal paths, these may be separately dimensioned and optimized.

In a further advantageous embodiment of the invention, the variable to be measured is passed directly into a first filter for selecting harmonic frequency components, and into a second filter, connected in parallel, for selecting the base frequency of the variable to be measured. The attenuating members are disposed to follow in series the two filters to which they are assigned. The filters are preferably designed to be passive filters. Owing to this design, an extremely high dynamic ratio of the system is achieved. The linear, passive filter components which are resistant to overload are located at the input of the circuit. Only the spectral components needed in each case are passed, so that only low signal levels are passed to subsequent active circuit components such as amplifiers or attenuating members. Thus, an overloading of these components, which may lead to undesired harmonics, for example, and thus to a falsification of the result of measurement, is avoided.

In another advantageous embodiment of the invention, the variable to be measured is passed directly into the first filter for selecting harmonic frequency components, with a second attenuating member to follow in series. Parallel to the first filter, the variable to be measured is passed into a first adjustable attenuating member to diminish the actual variable to be measured. This embodiment too offers an improved dynamic ratio, because the second attenuating member is supplied exclusively with the low-level signals of the harmonic frequency components, without the high levels of the base frequency.

In another advantageous embodiment of the invention, a track & hold circuit is provided. During the cutting, this circuit allows the instant signal values to pass without hindrance. If an end of cutting is signaled to this circuit, then it stores the last signal value until cutting is resumed. This kind of intermediate storing of the instant values is particularly expedient for a timing sequence that includes brief interruptions, such as that of coagulating and cutting, in which short periods of cutting and coagulation occur alternately. A track & hold circuit of this kind is preferably located at the input of the arrangement, or directly following the sampling tap of the generator. Variable-gain amplifiers with integrated behavior, in particular, should also preferably be equipped with a track & hold circuit. One or a plurality of track & hold circuits may be installed at various locations, depending upon the design of the circuit.

In the following the invention will be described by way of example, without limitation of the general inventive concept, with the aid of examples of embodiment with reference to the drawings.

DETAILED DESCRIPTION OF THE EMBODIMENTS

Figure 1:
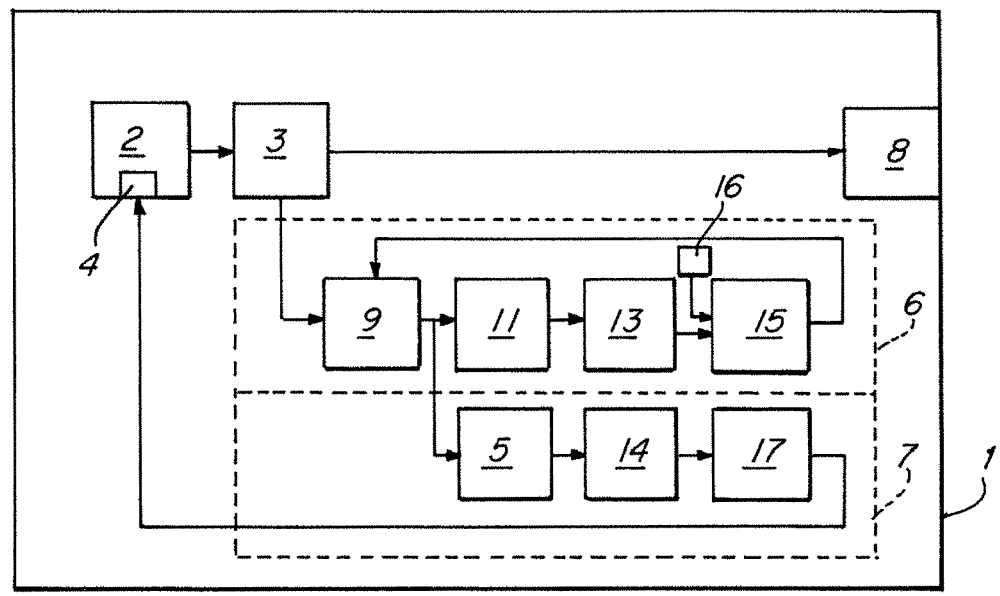
FIG. 1 schematically shows in a general form a device in accordance with the invention.

FIG. 1 illustrates an example of a device according to the invention. A generator 1 for high-frequency surgery (high-frequency-surgery generator) comprises a power generator 2 for supplying high-frequency power to output terminals 8. Connected to the output circuit is a sampling tap 3 serving to couple out a variable to be measured which corresponds to the output voltage or the output current of the power generator. This sampling tap may be incorporated in the power generator itself and may, for example, tap the voltage at an output transformer. However, it is of greater advantage to dispose it as closely as possible to the output terminals, in order to detect signals which are affected as little as possible by internal interference or parasitic couplings. The output variable selected to be measured depends on the design of the output circuits of the power generator and the load connected to the output terminals. However, a measurement of current has proved to be especially advantageous, because in the case of electric arcs the signal amplitudes of the harmonics are usually the largest.

The variable to be measured is passed from the sampling tap 3 to the standardizing circuit 6 which performs a suitable standardization of harmonic frequency components of the base frequency. These signals are then passed to the power generator 2 via means for scaling the harmonic frequency components, and via an input 4, to control an output variable. A controllable output variable is, for example, the power, the current, and also the voltage of the power generator. A particularly stable performance is obtained when the voltage of the power generator is controlled, because for the same tissue the voltage needed for cutting is independent from the electrode geometry, the depth of cutting and the speed of cutting. This means that a new value of the voltage need be set only when there is a change of the nature of the tissue. In this case therefore the regulating action is smallest. Thus the most stable regulation is achieved.

In this example the signals from the sampling tap 3 are passed by means of a first settable attenuating member 9 to a filter 11 for selecting the base frequency of the variable to be measured. The signals filtered in this manner are supplied to a controlled-gain amplifier 15 via a first rectifier 13. This compares the signals with a given desired value 16 and sets appropriate control signals for the first settable attenuating member for setting the attenuation. By means of the controller, the magnitude (amplitude, effective value, etc.) of the signal is regulated on the base frequency to a constant value corresponding to the desired value.

A filter 5 for selecting harmonic frequency components is also supplied with the output signals of the first attenuating member 9. Thus, the harmonic frequency components are diminished in the same way as is the base frequency by the first attenuating member 9 and therefore also standardized with the same standardizing factor k. The output signals from the filter 5 are further processed in a second rectifier 14 to be rectified, and in a following amplifier, and are subsequently passed to the power generator 1 by means of the input 4. In many cases the amplifier 17 may also be omitted. It serves here merely for an impedance matching or scaling with a constant factor in order to match the output signal of the rectifier to the power generator.

Figure 2:
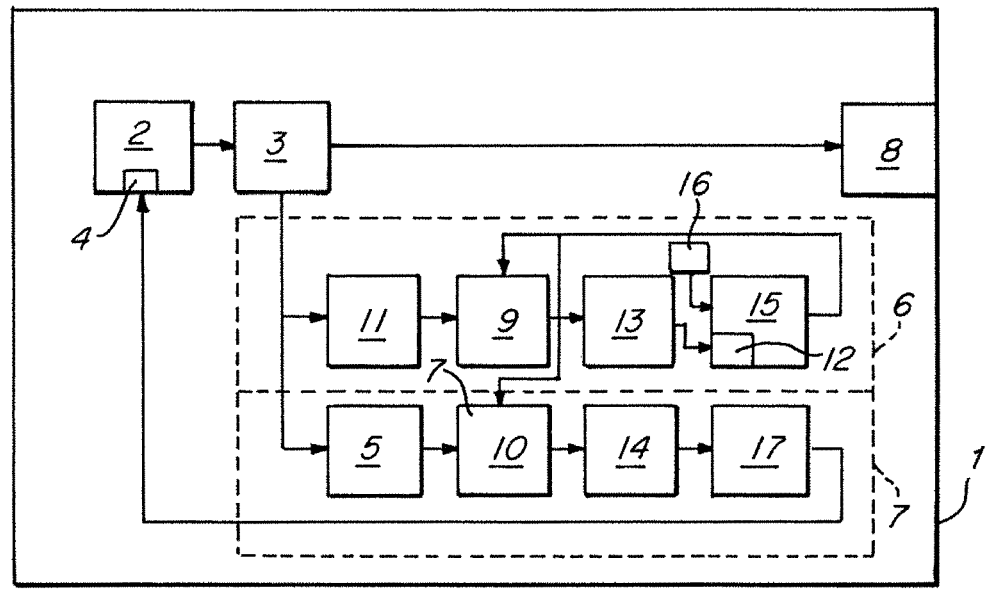
FIG. 2 shows as an example an embodiment with a particularly high dynamic ratio.

FIG. 2 illustrates an embodiment of the invention having a particularly high dynamic ratio.

In this, the output signal of the sampling tap 3 is passed directly to the filter 11 for selecting the base frequency of the variable to be measured, and also to the filter 5, connected in parallel, for selecting harmonic frequency components. Thus, two separate signal paths are obtained for the base frequency and for the harmonics. These may now be treated separately according to the signal amplitudes occurring. Thus there is a substantially smaller danger of producing harmonics by an overloading of circuit components. In the first signal path the base frequency filtered away by the filter 11 is passed on to the controlled-gain amplifier 15. This now controls in parallel the first settable attenuating member 9 and also the second settable attenuating member 10. Thus, both attenuating members have the same, or at least proportional, attenuation factors. The harmonic components diminished in this manner by the second settable attenuating member 10 are passed on via a second rectifier 14 and an optional amplifier 17 to the power generator 2 by means of the input 4 for control. In order to ensure satisfactory regulation even with pulsed or interrupted cutting operations, a track & hold circuit 12 is provided. This is preferably disposed at the input of the controlled-gain amplifier.

Figure 3:
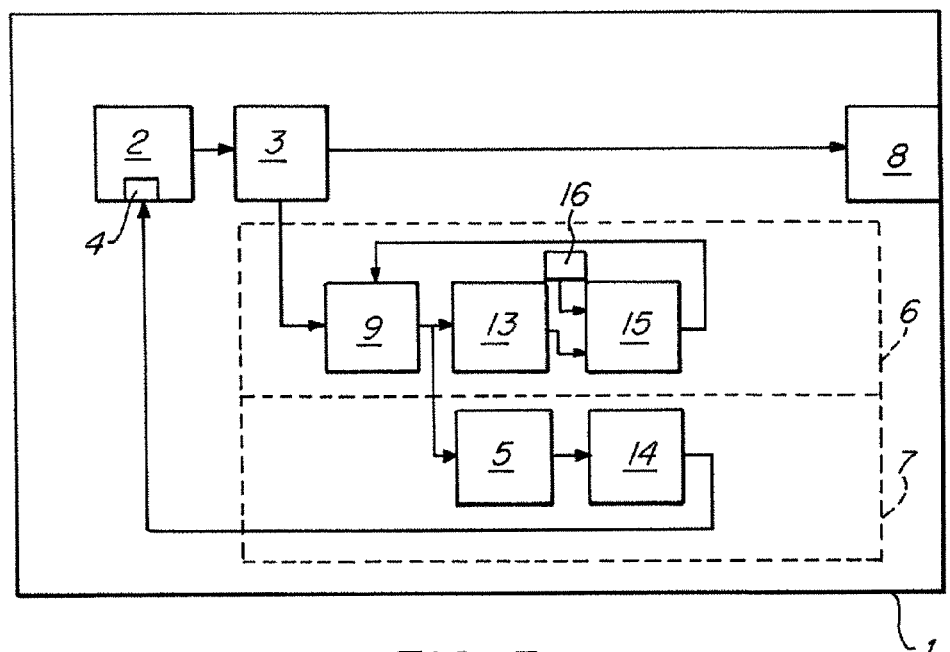
FIG. 3 shows as an example a particularly simple embodiment of the invention.

In FIG. 3 another embodiment of the invention is illustrated, which can be implemented with particularly small outlay. In this, as distinct from FIG. 1, the filter 11 for selecting the base frequency of the variable to be measured, and also the amplifier 17, have been omitted. If the variable to be measured contains only few harmonic components together with the signals of the base frequency, then the filter 11 may be omitted without any substantial drawbacks arising.

LIST OF REFERENCE SYMBOLS 1 high-frequency generator
2 power generator
3 sampling tap
4 input for setting an electrical output variable
5 filter for selecting harmonic frequency components
6 standardizing circuit
7 means for scaling the harmonic frequency components
8 output terminals
9 first settable attenuating member
10 second settable attenuating member
11 filter for selecting the base frequency of the variable to be measured
12 track & hold circuit
13 first rectifier
14 second rectifier
15 controlled-gain amplifier
16 desired value
17 amplifier

What is claimed is:

1. High-frequency generator for high-frequency surgery, comprising:
    a power generator for supplying high-frequency energy at a base frequency;
    a sampling tap for receiving the value of a variable to be measured, corresponding to an output voltage or an output current of said power generator; and
    said power generator having at least one input for setting a magnitude of an electrical output parameter selected from an output voltage, an output current, and an output power;
    wherein
    a standardizing circuit is provided for determining a standardizing factor k in such manner that the measured variable or a proportion of the basic frequency in the measured variable, multiplied by the standardizing factor, corresponds to a given desired value;
    a first filter is provided for selecting harmonic frequency components above a base frequency from the variable to be measured;
    means are provided for scaling the harmonic frequency components with the standardizing factor k; and
    for controlling the power generator, a signaling of scaled harmonic frequency components to the power generator by means of the input is provided in such manner that with an increase of an amplitude of the scaled harmonic frequency components, the output voltage, the output current or the output power of the power generator is reduced.

2. High-frequency generator according to claim 1, wherein the standardizing circuit comprises a first rectifier for determining a peak value of the variable to be measured, and determines the standardizing factor k with respect to the peak value of the measured variable.

3. High-frequency generator according to claim 1, wherein the standardizing circuit comprises a first rectifier for determining an effective value or a mean value of the measured variable, and determines the standardizing factor k with respect to the effective value of the measured variable.

4. High-frequency generator according to claim 1, wherein the standardizing circuit comprises a regulator circuit for diminishing the measured variable by means of a first settable attenuating member so that it corresponds to a given desired value.

5. High-frequency generator according to claim 4, wherein the first filter for selecting harmonic frequency components is disposed in series with the first settable attenuating member, so that the entire measured variable including the harmonic frequency components is diminished by the first settable attenuating member.

6. High-frequency generator according to claim 4, wherein, for diminishing the harmonic frequency components, a second settable attenuating member is provided, which is controlled parallel to the first settable attenuating member, so that attenuations by the first and second attenuating members correspond to each other.

7. High-frequency generator according to claim 6, wherein the variable to be measured is passed directly into the first filter for selecting harmonic frequency components, and into a second filter connected in parallel therewith for selecting the base frequency of the variable to be measured, and that the respectively assigned settable attenuating members are disposed in series following the first and second filters.

8. High-frequency generator according to claim 6, wherein the variable to be measured is passed directly into the first filter for selecting harmonic frequency components followed in series by the first attenuating member, and into the second attenuating member connected in parallel therewith for diminishing the variable to be measured itself.

9. High-frequency generator according to claim 1, wherein a track & hold circuit is provided, which passes actual signal values during a cutting operation, and in cases of brief interruptions of the cutting operation, stores a last signal value until the cutting operation is resumed.

10. A high-frequency generator for high-frequency surgery, comprising:
    a power generator supplying high-frequency energy at a base frequency and having:
        a sampling tap for measuring a variable (MV) related to an output voltage or an output current;
        at least one input for setting a magnitude of an electrical output parameter selected from the group consisting of: an output voltage, an output current, and an output power;
    a constant value (C) defined as a voltage or a current;
    a standardizing circuit receiving the measured variable and generating a standardizing factor k by dividing the constant value (C) by the measured variable (MV) or by a proportion of the basic frequency in the measured variable;
    a filter selecting harmonic frequency components above a base frequency from the measured variable; and
    a controller scaling the harmonic frequency components with the standardizing factor k;
    said scaled harmonic frequency components send to said at least one input such that with an increase of an amplitude of the scaled harmonic frequency components, the output voltage, the output current or the output power of the power generator is reduced.

* * * * *